Figure 1:
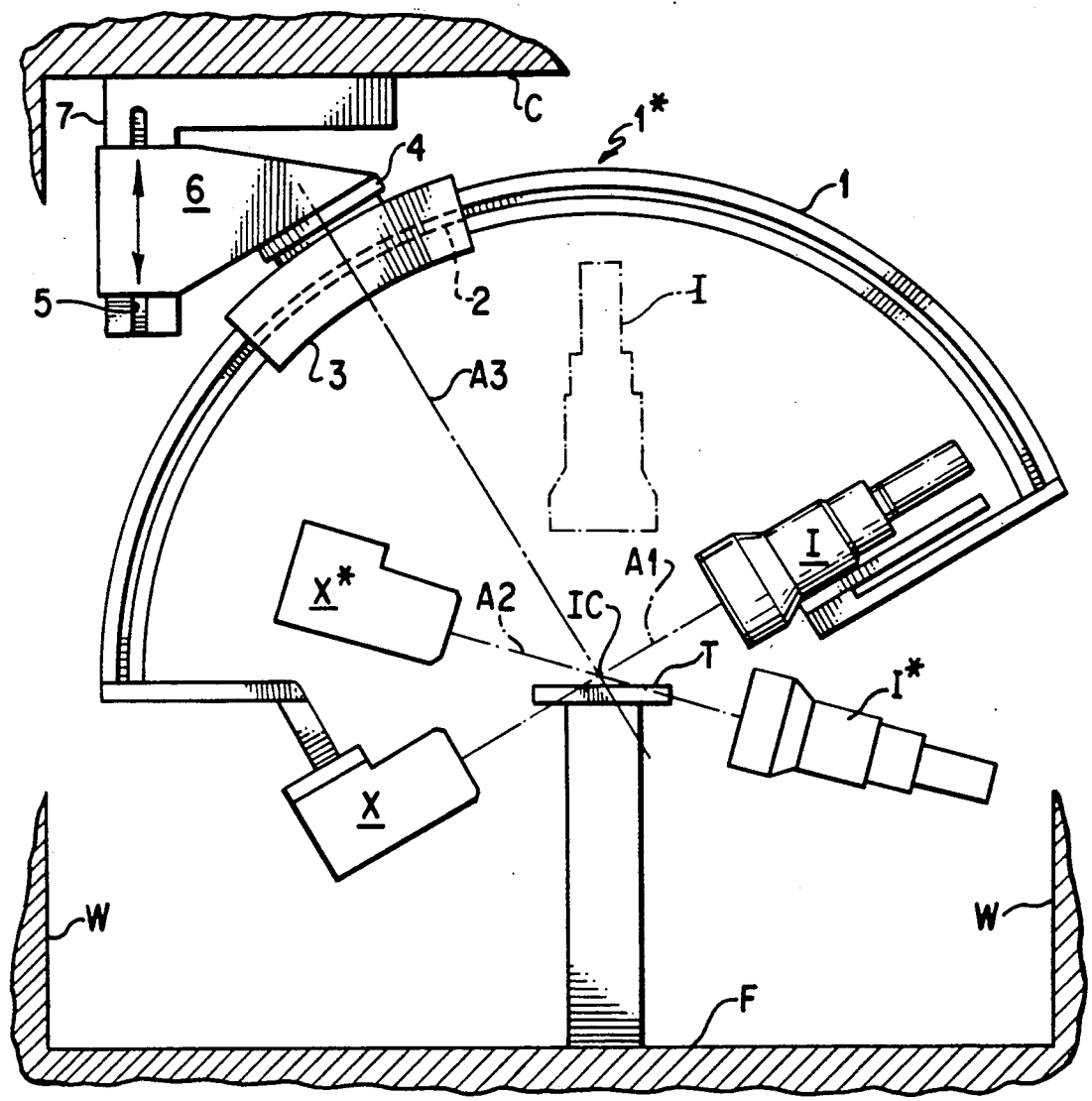

United States Patent [19]

Grady

[11] Patent Number: 5,052,036
[45] Date of Patent: Sep. 24, 1991

[54] X-RAY STAND WITH LATERALLY INCLINED ROTATION AXIS

[76] Inventor: John K. Grady, XRE Corporation, 300 Foster St., Littleton, Mass. 01460

[21] Appl. No.: 503,255

[22] Filed: Apr. 2, 1990

[51] Int. Cl.$^5$ .............................................. H05G 1/02
[52] U.S. Cl. .................................... 378/197; 378/193; 378/205; 378/11; 378/62
[58] Field of Search .................... 378/62, 11, 193, 195, 378/1, 198, 205-208

[56] References Cited

U.S. PATENT DOCUMENTS

| | | | |
|---|---|---|---|
| 3,670,163 | 6/1972 | Lajus | 378/196 |
| 3,892,967 | 7/1975 | Grady et al. | 378/197 |
| 4,426,725 | 1/1984 | Grady | 378/196 |
| 4,716,581 | 12/1987 | Barud | 378/198 |
| 4,741,015 | 4/1988 | Charrier | 378/196 |
| 4,756,016 | 7/1988 | Grady et al. | 378/197 |
| 4,868,845 | 9/1989 | Koropp | 378/204 |
| 4,922,512 | 5/1990 | Lajus et al. | 378/197 |
| 4,961,214 | 10/1990 | Van Endschot et al. | 378/197 |

OTHER PUBLICATIONS

Siemens-Elema AB, Biplane System for Cardiovascular Examination and International Technique.
Philips Meidcal Systems Inc., Poly Diagnostic/Lateral ARC, Apr. 1983.
CGR, Angiomax, Sep. 1983.

Primary Examiner—Edward P. Westin
Assistant Examiner—Kim-Kwok Chu
Attorney, Agent, or Firm—James H. Grover

[57] ABSTRACT

An X-ray stand includes a fixture attached to the ceiling surface floor surface or side wall surface of a hospital room. A support is connected to the fixture with a rotary bearing connected to a circular track. An arcuate carriage sliding in the track has a radiation source and receptor respectively at its ends which are aligned on a radiation axis through a patient position. The rotational axis of the bearing is inclined at a substantial angle to the fixture and to the wall to which the fixture is attached so that, when the one end of the arcuate carriage is in a position near the ceiling or other wall, rotation around the bearing axis will rotate the radiation axis through substantially different angles through the patient position.

13 Claims, 1 Drawing Sheet

X-RAY STAND WITH LATERALLY INCLINED ROTATION AXIS

BACKGROUND OF THE INVENTION

Many cardiological X-ray examinations require exposure of the heart of a patient from different spherical angles toward his support table. Stands supporting an X-ray source and an X-ray receptor on a radiation axis capable of being angulated about the patient table are well known as shown in U.S. Pat. No. 3,892,967. In some procedures two sets of X-ray source and receptor are used to allow biplane exposures of the patient from two angles without moving either radiation set, as shown in U.S. Pat. No. 4,426,725. Both single plane and biplane X-ray stands must be accommodated within the finite dimensions between the ceiling, floor and side walls of the hospital examination room, and at the same time must be capable of rotation through substantial solid angles from wide spherical angles toward the table.

One prior system, known as BICOR, manufactured by Siemens-Elema, Solna, Sweden suspends an X-ray set of source and receptor from a ceiling fixture supporting a bearing with a vertical axis of rotation for a curved track. Through the track slides a C-shaped, arcuate support with an X-ray source and receptor at opposite ends of the C. The problem with this system is that as the arcuate support swings the radiation axis toward a vertical plane, angulation of the radiation axis about the nearly parallel vertical axis of the bearing produces negligible angulation with respect to the patient, and does not provide the desired exposure of significantly different planes in the patient. One answer to the problem is provided by the Lateral ARC X-ray stand of Philips Medical Systems, Inc., Shelton, Connecticut, but at the expense of mounting two C-arms concentrically, one within the other, thereby increasing the floor to ceiling extent of the stand unacceptably beyond the finite dimensions normally available in hospitals, and seriously reducing the source-to-image-distance (SID) available between the X-ray source and receptor on the inner C-arm.

Accordingly it is the object of the present invention to provide an X-ray stand with which the radiation axis can be inclined close to vertical and yet be rotated at that inclination to substantially different angles in a plane through the patient, which also maximizes the length of the radiation axis between source and receptor with respect to the available dimensions of the hospital room, which maximizes the diameter of the single C-arm and the SID through the patient, and which allows greater freedom of movement of the C-arm around the patient table and free access of medical personnel to the patient.

SUMMARY OF THE INVENTION

According to the invention an X-ray stand for installation on the ceiling, floor or side walls of a hospital room of finite dimensions, comprises a fixture for attachment to the ceiling, floor or side wall, a support connected to the fixtue holding a bearing with a rotational axis, a circular track mounted on the bearing for rotation on the axis, an arcuate carriage received in the track so as to slide between end positions, and a primary radiation set of X-ray source and receptor disposed at the ends of the carriage and aligned on a radiation axis through the horizontal plane of a patient position; wherein the rotational axis of the bearing is inclined at a substantial angle to the fixture and wall, so that the arcuate carriage in its end positions can be rotated with the track to substantially different angles through the patient position while maximizing the radius of the arcuate carriage with respect to the finite dimensions of the room between the ceiling and floor walls.

DRAWINGS

FIG. 1 is of an X-ray stand showing a first radiation set according to the invention in side elevation, and a second X-ray set diagrammatically.

DESCRIPTION

Shown in FIG. 1 is a biplane X-ray system for examining a patient on a table T resting on the floor F of a hospital room having a ceiling C, a floor F and side walls W. The dimensions between the ceiling and floor, and the side walls of a hospital room are determined prior to building construction within finite limits and not feasibly alterable thereafter, although the X-ray stand Is not ususally installed until after completion of the hospital building. Thus the X-ray equipment must designed to fit within the dimensions of the available room.

A first radiation set of an X-ray tube source X and an X-ray receptor I, for example an X-ray image intensifier, are aligned on a first radiation axis A1 passing through an isocenter IC above a patient table T. The source X and receptor I are mounted on brackets at opposite ends of an arcuate C-arm carriage 1 which slides in a circular track 2 within a housing 3 between end positions with the source or receptor adjacent the housing. The track housing 3 is connected by a rotary bearing 4 to a support 6 adjustable vertically up a guide 5 on a fixture 7 attached to the ceiling C.

For biplane examination a second radiation set of source X* and receptor I* is combined with the above described primary X-ray stand. The secondary set may be like those shown in U.S. Pat. Nos. 3,892,967, 4,426,725 or 4,756,016, or like the primary set, and may be mounted on the floor as shown, or otherwise, and have a secondary radiation axis A2 through the isocenter IC.

The rotational axis A3 of the C-arm bearing 4 normally intersects the isocenter IC cf the radiation axis A1, and of the secondary radiation axis A2 in a biplane system as shown. This permits exposures of a patient at the isocenter IC by the primary X-ray set X,I from various angles in a first plane throughout 360 degrees when its radiation axis A1 is at right angles to the rotatation axis A3.

In prior X-ray stands the range of exposure angles in a second plane normal to the first plane became negligible as the C-arm 1 swung the primary radiation axis A1 toward vertical, that is with the image intensifier I close to the track housing 3.

According to the invention, the rotational axis A3 of the bearing 4 on the support 6 between the ceiling fixture 7 and the circular track housing 3 is inclined at a substantial angle to the vertical extent of the fixture 7 and to the horizontal ceiling wall C, for example 30 to 40 degrees. Such an inclination midway between the vertical and the horizontal, with a mid position of the primary radiation carriage in the track close to the position shown, is close to the angle usually used in cardiac examinations. And it allows over 90 degrees of angulation in the plane of FIG. 1, in addition to the 360 degrees out of the plane of FIG. 1, thus permitting exposures in all useful planes of the patient.

In addition to increasing the available spherical angulation through the patient position with a single C-arm, the inclination of the rotation of the bearing 4 also causes the circular track 2 of the housing 3 and the arcuate carriage 1 to be inclined such that the track 2 and carriage 1 always extend upwardly toward the ceiling wall C. Therefor the uppermost part 1* of the carriage is closer to the ceiling than is the track 2. This compensates in part for the vertical space needed for the ceiling fixture 7 and integral support 6, and thereby makes possible a carriage 1 of greater radius than with the prior vertical rotation axis, affording a maximum SID and freer access to the patient table.

It should be understood that the present disclosure is for the purpose of illustration only, and that the invention includes all modifications and equivalents falling within the appended claims.

I claim:

1. An X-ray stand for installation on the ceiling surface, floor surface or side wall surface of a hospital room of finite dimensions for examination of a patient comprising:
   a fixture for attachment to one of the surfaces;
   a support connected to the fixture holding a bearing with a rotational axis;
   a circular track mounted on the bearing for rotation on the axis;
   an arcuate carriage received in the track so as to slide on a circular path between end positions on the track; and
   a primary set of a radiation source and a radiation receptor disposed at the ends of the carriage and aligned on a primary radiation axis through a fixed isocenter at the patient position;
   wherein the rotational axis of the bearing is fixed at an inclination significantly more than zero and less than ninety degree to the fixture and surface to which the fixture is attached, so that the arcuate carriage in its end positions can be rotated with the track to substantially different angles of the radiation axis through the fixed isocenter at the patient position, while maximizing the radius of the arcuate carriage with respect to the finite dimensions of the room between the ceiling and floor walls and providing substantial change in the radiation angle through the patient by rotation about the bearing axis with one carriage end adjacent the bearing axis.

2. An X-ray stand according to claim 1 wherein the fixture is mounted on a horizontal ceiling wall.

3. An X-ray stand according to claim 1 comprising means for mounting the fixture on a horizontal ceiling wall.

4. An X-ray stand according to claim 1 wherein the stand includes only one arcuate carriage.

5. An X-ray stand according to claim 1 wherein the carriage is a C-shaped arm.

6. An X-ray stand according to claim 1 wherein the stand includes only one C-arm.

7. An X-ray stand according to claim 1 wherein a part of the arcuate carriage is located closer to the surface on which the bearing is mounted than is the circular track.

8. An x-ray stand according to claim 7 wherein the fixture is mounted on a horizontal ceiling wall.

9. An X-ray stand according to claim 7 wherein the carriage is a C-shaped arm.

10. An X-ray stand according to claim 7 wherein the stand includes only one arcuate carriage.

11. An X-ray stand according to claim 1 wherein the bearing support is slidingly mounted on the fixture.

12. An X-ray stand according to claim 1 in combination with a second stand with a secondary radiation axis disposed at an angle to the primary radiation axis and intersecting the primary radiation axis at a common isocenter.

13. An X-ray stand according to claim 1 wherein the arcuate carriage slides about an axis normal to the rotational axis of the bearing.

* * * * *